United States Patent [19]

Tsuchihashi et al.

[11] B 4,001,276
[45] Jan. 4, 1977

[54] α-ALKYL(OR ARYL)THIO-5-HYDROXYTRYPTOPHAN DERIVATIVE AND THE PREPARATION PROCESS THEREOF

[75] Inventors: Genichi Tsuchihashi, Tama; Katsuyuki Ogura, Sagamihara, both of Japan

[73] Assignee: Sagami Chemical Research Center, Japan

[22] Filed: Feb. 26, 1974

[21] Appl. No.: 446,107

[44] Published under the second Trial Voluntary Protest Program on March 9, 1976 as document No. B 446,107.

[30] Foreign Application Priority Data

Mar. 1, 1973  Japan .............................. 48-23734

[52] U.S. Cl. ............. 260/326.12 R; 260/326.14 T; 260/340.6; 260/340.9; 260/455 R
[51] Int. Cl.² ....................................... C07D 209/20
[58] Field of Search ......... 260/326.12 R, 326.12 A, 260/326.14 T

[56] References Cited
OTHER PUBLICATIONS

Sundberg, "The Chem. of Indoles," pp. 234–235, (1970).
Howlihan, "Indoles," part I, pp. 246–248, part II, p. 221, (1972).

*Primary Examiner*—Elbert L. Roberts
*Assistant Examiner*—S. P. Williams
*Attorney, Agent, or Firm*—Wenderoth, Lind & Ponack

[57] ABSTRACT

As a novel compound, an α-alkyl(or aryl)thio-5-hydroxytryptophan derivative and the preparation process thereof are disclosed. Said novel compound is readily convertible to 5-hydroxytryptophan having a versatile utilization.

2 Claims, No Drawings

α-ALKYL(OR ARYL)THIO-5-HYDROXYTRYPTOPHAN DERIVATIVE AND THE PREPARATION PROCESS THEREOF

This invention relates to an α-alkyl (or aryl) thio-5-hydroxytryptophan derivative of the formula

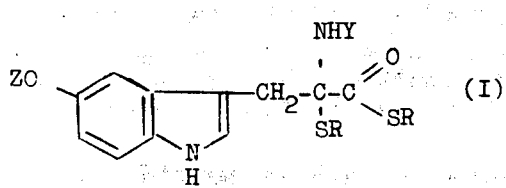

in which R is an alkyl or aryl group, Y is a protective group for amino function and Z is a protective group for hydroxy function,
and also to the preparation process thereof.

The compound of the abovementioned formula (I) is a novel compound which can very effectively be used as the intermediate for the production of a variety of organic compounds. By using this compound, for instance, 5-hydroxytryptophan known widely as effective medicine for depression and mongolian idiocy or as antioxidant for foods can readily be obtained.

As some of the typical methods conventionally employed for the preparation of 5-hydroxytryptophan, an oxidizing process of 2,3-dihyrotryptophan derivatives (German Offenlegungs Schrift No. 2,152,088) or a process by means of enzym, produced by microorganisms (Japanese Patent Publication No. 34,152/1972) can be named. These methods inevitably involve a complicated non-chemical zymotechnical step which requires a culture of specific bacilli under extremely specified conditions. These methods therefore lack in versatility and are unsuited for the production on a large scale. In the former method, the starting 2,3-dihydrotryptophan is to be synthesized by reducing tryptophan prepared by zymotechnics, while the latter method requires the cultivation of very specific bacilli.

In contrast thereto, the compound of the formula (I) can easily be synthesized chemically and can further be converted easily and effectively to 5-hydroxytryptophan by known chemical reactions such as ester interchange with alcohols R''OH, reductivedesulphurization with concomitant cleavage of the protective group Z, splitting-off of the protective group Y and the like as illustrated in the undermentioned reaction formula. The reductive desulphurization can be carried out by using, for example, active nickel and the splitting-off of the protective group Y can be made by acid hydrolysis.

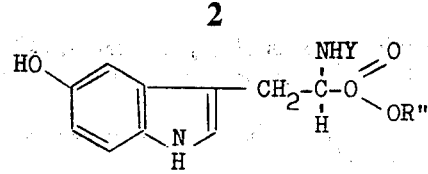

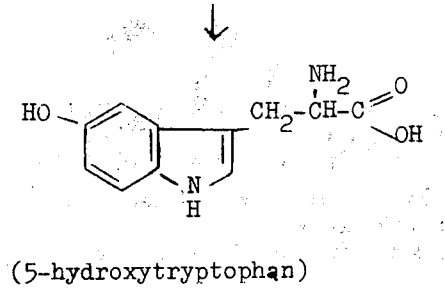

(5-hydroxytryptophan)

The two R groups in the aforementioned formula (I) may be any alkyl or aryl group. On the preparation of 5-hydroxytryptophane from the compound of the formula (I), the two —SR groups are split off as illustrated in the above reaction formulae. Hence, it does not count much what specific groups the two Rs are. However, it is preferred that the two Rs be lower alkyl groups having 1 – 3 carbon atoms, especially methyl groups respectively. For, among the compound of the later-appearing formula (II) which is the starting compound of the compound of the formula (I) such compounds are most readily available in which the two Rs are lower alkyl groups having 1 – 3 carbon atoms.

In the said formula (I), Y is a protective group for amino function and Z is a protective group for hydroxy function. Protective groups in this case means an inert group which replaces one active hydrogen of the amino or hydroxy group so as to temporarily restrain the reactivity of these groups. Protection of amino group and hydroxy group by the protective groups are needed to prevent undesired side-reactions in the synthesis of the compound of the formula (I) and also in the converting of the compound to 5-hydroxytryptophan. Protective groups for amino and hydroxy groups are known widely in the chemical art. Specific examples of the protective group for the amino function are acetyl, trifluoroacetyl, benzyloxycarbonyl and p-toluenesulfonyl groups and the examples of the protective group for the hydroxy group include alkyl, benzyl, benzoyl and acetyl groups.

According to the present invention, it is found that the compound of the formula (I) can easily be prepared by reacting a thiol ester of the formula (II)

wherein R and Y are the same as already defined and X is

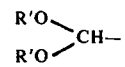

or $$\begin{matrix} R'O \\ R'O \end{matrix} \!\!> CH-$$

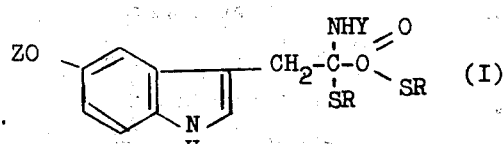

in which R' is a lower alkyl group, the two R' groups together being capable of forming an alkylene group,
with a p-hydroxyphenylhydrazine derivative of the following formula (III)

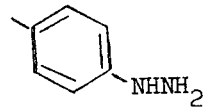  (III)

in which Z is the same as already defined,
under acidic conditions.

When X in the above formula (II) is a formyl group or

the compound is a 4-formyl-2-amino-2-alkyl(or aryl)-thiolactic acid thiol ester wherein one hydrogen atom in the amino group is substituted by the protective group. When X is

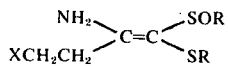

further, the compound corresponds to an acetal of the abovementioned formyl compound and is 5,5-dialkoxy-(or alkylenedixoy)-2-amino-2-alkyl(or aryl)thiovaleric acid thiol ester wherein one hydrogen atom of the amino group is substituted by the protective group. It is preferred that the two R' groups be alkyl groups having 1 – 3 carbon atoms or the two R' groups together can form an ethylene group.

The thiol ester of the formula (II) is also a novel compound synthesized for the first time by the inventors of the present invention and the preparation process thereof is disclosed in our copending patent application Ser. No. 396,366 filed Sept. 12, 1973.

The process comprises reacting a nitrile of the formula, $XCH_2CH_2CN$ with a sulfoxide of the formula, $$RSCH_2SR \atop \| \atop O$$

in the presence of a metalating agent, and contacting the resulting reaction mixture with a protic material to obtain an enaminosulfoxide of the formula,

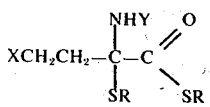

followed by reacting the thus obtained enaminosulfoxide with an acylating agent to produce a thiol ester of the formula $$XCH_2CH_2-\overset{NHY}{\underset{SR}{C}}-C\overset{O}{\underset{SR}{\diagdown}}$$

In the above formulae, R, X and Y are the same as already defined.

Another starting material for the preparation of the compound of the formula (I) is the compound expressed by the formula (III) which is a compound derived from known phydroxyphenylhydrazine whose hydroxy group is protected by the aforementioned protective group. Mineral acid salts of the said hydrazine derivatives can also be used as the preferable starting material.

It is assumed that the formation of the compound of the formula (I) by the reaction of the compound (II) with the compound (III) proceeds in line with the following reaction formulae:

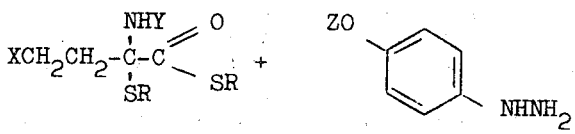

The reaction of the compound of the formula (II) with the compound of the formula (III) is preferably carried out in the presence of a solvent. As the solvent, polar solvents are preferred such as water, methanol, ethanol, acetic acid and mixtures of these compounds. Together with these polar solvents, non-polar solvents such as ether, methylene chloride, benzene, chloroform and the like can be used in the form of mixture.

The reaction is carried out under the acidic conditions. As the compounds which provide the acidic conditions, mineral acids such as hydrochloric acid and sulphuric acid, organic acids such as acetic acid, p-toluenesulfonic acid and sulfosalicylic acid, Lewis acid such as zinc chloride, can all be used. When a mineral acid salt of the hydrazine compound of the formula (III) is used as the starting material, the acid conditions can be maintained in the reaction system without adding the abovementioned acid-donating compound. The amount of the acid to be added is sufficient in such a small amount as 0.1 mol equivalent, but preferably, it is equimol or more to the starting compound (III).

The reaction temperature is usually in the range from room temperature up to 150°C and preferably in the range of 40° to 150°C.

The present invention will be described further in detail by the following working and referential examples.

REFERENTIAL EXAMPLE 1

[Synthesis of the starting compound of the formula (II)]

a. Formaldehyde dimethyl mercaptal S-oxide (2.370g) was dissolved in 20 ml of tetrahydrofuran, to which 475 mg of sodium hydride was added under ice cooling. Then, the system was stirred for 50 minutes at 0°C and another 50 minutes at room temperature. Under ice cooling again, 3.73 ml of 4,4-dimethoxybutylonitrile was added dropwise to the system and subsequently, the system was stirred for 18 hours at room temperature and 23 hours at 50°–55°C. After ice cooling the system again, 30 ml of methylene chloride and 1 ml of water were added and the system was then stirred for 3 hours at room temperature. After drying with anhydrous sodium sulfate, the reaction mixture was filtered and the solvent was removed under reduced pressure. By separating the residue by column chromatography [chromatographic adsorbents: "Florisil" (a tradename, Floridin Company, USA), eluvent: methylene chloride, ethyl acetate, and methanol], 457 mg of formaldehyde dimethyl mercaptal S-oxide and 4.332 g of crystals were obtained. The resulting crystals were dissolved in hot methylene chloride to remove insoluble substances and concentrated under reduced pressure to afford 3.7g of 5,5-dimethoxy-2-aminomethylsulfinyl-1-methylthio-1-pentene having a melting point of 86°–87°C. The yield was 76.5%.

IR(KBr): 1008, 1627, 3150, 3273, 3400 cm$^{-1}$
NMR(CDCl$_3$): There were two geometrical isomers of E and Z.
One isomer:
δ  2.29s(3H), 2.65s(3H), 3.37s(6H), 1.65–3.15m(4H), 4.40t(1H, J = 5.3cps), 5.53 diffused peak (2H)
Another isomer:
δ  2.19s(3H), 2.74s(3H), 3.37s(6H), 1.65–3.15(4H), 4.45t(1H, J = 5.3 cps), 5.90 diffused peak (2H)
Analyzed as C$_9$H$_{19}$O$_3$S$_2$N:
Calculated: C 42.66; H 7.56; S 25.31
Found: C 42.54; H 7.61; S 25.15 b. About 1 ml of acetic anhydride was added to 300 mg of 5,5-dimethoxy-2-amino-1methylsulfinyl-1methylthio1-pentene and the mixture was left standing fro 16 hours at room temperature. Then, acetic anhydride and acetic acid were removed off under reduced pressure to afford crystals. The so obtained crystals were recrystalized from a carbon tetrachloride - cyclohexane - benzene system to afford 229 mg of 5,5-dimethoxy-2-acetylamino-2-methylthiovaleric acid methanethiol ester as pale-yellow crystals having a melting point of 101° – 120°C. The mother liquid was concentrated under reduced pressure and was passed through a column ("Florisil," methylene chloride, ethyl acetate, and methanol) to separate additional 25 mg of 5,5-dimethoxy-2-acetylamino-2-methylthiovaleric acid methanethiolester and the yield amounted to 72.7%.

IR(KBr): 1668 – 1692, 3272 cm$^{-1}$
NMR(CDl$_3$): δ1.96s(3H), 2.07s(3H), 2.38s(3H), 1.2 – 2.3 m(4H), 3.32s(6H), 4.37t(1H, J = 5.6cps), 6.72 diffused peak(1H)
Analyzed as C$_{11}$H$_{21}$O$_4$NS$_2$:
Calculated: C 44.72; H 7.17; S 21.71
Found: C 44.46; H 6.88; S 21.64

EXAMPLE 1 p-Benzyloxyphenylhydrazine hydrochloride (332 mg) and 5,5-dimethoxyamino-2-methylthiovaleric acid methanethiol ester (351 mg) were added to 15 ml of a mixture of acetic acid and water (1 : 3) and stirred for 13 hours at room temperature. After stirring the system for 2 hours at 80°C, 447 mg of β-(5-benzyloxyindolyl-3)-α-acetylamino-α-methylthiopropionic acid methanethiol ester was extracted as a pale-yellow solid in the yield of 87.5%. The resulting solid was recrystallized from ethanol to afford colorless crystals having a melting point of 201° – 202°C (decompose).

IR(KBr): 3350, 3180, 1675, 1652 cm$^{-1}$
NMR(CD$_3$SOCD$_3$): δ1.82s(3H), 1.98s(3H), 2.19s(3H), 3.37d(1H, J = 14Hz), 3.73d(1H,J = 14Hz), 5.04s(2H) 6.6 – 7.6m(9H), 8.30 broad (1H), 10.80 broad (1H)
Analyzed as C$_{22}$H$_{24}$N$_2$O$_3$S$_2$:
Calculated: C 61.65; H 5.65; S 14.97
Found: C 61.43; H 5.55; S 14.86

EXAMPLE 2 p-benzyloxyphenylhydrazine hydrochloride (332 mg) and 5,5-ethylenedioxy-2-acetylamino-2-methylthiovaleric acid methanethiol ester (350 mg) were added to 10 ml of a mixture of acetic acid and water (1 : 3) and the system was stirred for 3 hours at room temperature and for 2 hours at 80°C. By adding 15 ml of water to the system, 390 mg of β-(5-benzyloxyindolyl-3)-α-acetylamino-α-methylthiopropionic acid methanethiol ester was obtained as pale-yellow crystals in the yield of 77%.

EXAMPLE 3 p-Benzyloxyphenylhydrazine hydrochloride (332 mg) and 5,5-dimethoxy-2-acetylamino-2-methylthiovaleric acid methane thiol ester (351 mg) were added to 10 ml of ethanol and the system was stirred for 1 hour at room temperature and subsequently refluxed under heating for 2 hours. By adding 15 ml of water to the system, 309 mg of β-(5-benzyloxyindolyl-3)-α-acetylamino-α-methylthiopropionic acid methanethiol ester was obtained as pale-yellow crystals in the yield of 61%.

EXAMPLE 4 p-Benzyloxyphenylhydrazine (283 mg) and 5,5-dimethoxy-2-acetylamino-2-methylthiovaleric acid methanethiol ester (351 mg) were dissolved in 15 ml of a mixture solution of water and ethanol (1:1) and then 300 mg of p-tolenesulfonic acid was added to the reaction mixture. The system was stirred for 11 hours at room temperature and for 3 hours at 80°C. By adding 15 ml of water to the system, 263 mg of β-(5-benzyloxyindolyl-3)-α-acetylamino-α-methylthiopropionic acid methanethiol ester was separated by filtration in the yield of 52%.

EXAMPLE 5 p-Benzyloxyphenylhydrazine (283 mg) and 5,5-dimethoxy- 2-acetylamino-2-methylthiovaleric acid methanethiol ester (351 mg) were added to 15 ml of a mixture solution of ethanol and water (1 : 1) and further 162 mg of zinc chloride was added to the system. The reaction mixture was stirred for 10 hours at room temperature and 4 hours at 80°C and there extracted 224 mg of β-(5-benzyloxyindolyl-3)-α-acetylamino-α-methylpropionic acid methanethiol ester as pale-yellow solid in the yield of 44%.

EXAMPLE 6

Following the same procedures as in Example 5 except that 303 mg of sulfosalicylic acid was used instead of 162 mg of zinc chloride, 201 mg of β-(5-benzyloxyindolyl-3)-α-acetylamino-α-methylthiopropionic acid methanethiol ester was obtained in the yield of 39%.

EXAMPLE 7

By following the same procedures as in Example 1 except that 297 mg of 4-formyl-2-acetylamino-2-methylthiolactic acid methanethiol ester was used instead of 351 mg of 5,5-dimethoxy-2-acetylamino-2-methylthiovaleric acid methanethiol ester, 430 mg of β-(5-benzyloxyindolyl-3)-α-acetylamino-α-methylthiopropionic acid methanethiol ester was obtained in the yield of 84%.

REFERENTIAL EXAMPLE 2

[Synthesis of 5-hydroxytryptophan from the compound of the formula (I)]

β-(5-Benzyloxyindolyl-3)-α-acetylamino-α-methyl-thiopropionic acid methanethiol ester (449 mg) was added to 10 ml of ethanol and further 1 ml of triethylamine was added to the mixture. Then, the reaction mixture was refluxed for 17 hours. after condensation under reduced pressure and subsequent separation of the residue by column chromatography (silica gel, ethyl acetate), 353 mg of methyl β-(5-benzyloxyindolyl-3)-α-acetylamino-α-methylthiopropionate was obtained as colorless glass-like substance in the yield of 81.5%. Recrystallization of the substance from methanolwater afforded 287 mg of crystals.

Colorless-crystal: mp 178° − 179.5°C NMR(DMSO-$d_6$): δ 1.85s(3H), 2.03s(3H), 3.32d(1H, J—15Hz), 3.71d(1H, J—15 Hz), 5.09s(2H), 6.7–7.6m(9H), 8.29s(1H,NH), 10.82 broad s(1H, NH)

IR(KBr): 3360, 3200, 1736, 1600 cm$^{-1}$

Analyzed as $C_{22}H_{24}O_4N_2S$:
Calculated: C 64.05; H 5.87
Found: C 64.11; H 6.05

Raney nickel (3.5cc) was suspended in 10 ml of ethanol and 356 mg of methyl β-(5-benzyloxyindolyl-3)-α-aminoacetyl-α-methylthiopropionate was added to the mixture together with 20 ml of ethanol. Then, the reaction mixture was stirred for 1 hour at room temperature and thereafter filtered to remove insoluble substances. The residue was washed with 100 ml of ethanol and 50 ml of acetone and both the filtrate and the wash liquid were combined and concentrated under reduced pressure. By column chromatography (silica gel and acetone), 210 mg of methyl β-(5-hydroxyindolyl-3)-α-acetylaminopropionate as colorless glass-like substance in the yield of 90%.

NMR (DMSO-$d_6$): δ1.83s(3H), 3.02d(2H, J = 6Hz), 3.62s(3H), 4.57m (1H)$^{(a)}$, 6.62 d of d (1H, J=8.5, 2.5Hz), 6.82d(1H, J=2.5Hz), 7.07 broad s (1H)$^{(b)}$, 7.13d(1H, J=8.5Hz), 8.25 broad d (1H, J=8Hz)$^{(c)}$, 10.52 broad s (1H)$^{(c)}$ After D$_2$O treatment;
a. triplet J=6Hz;
b. sharp singlet
c. disappeared IR(KBr): 3350 (broad), 1736, 1650 cm$^{-1}$ The resulting product was then acetylated by a customary manner (acetic anhydride - pyridine). m.p. 175° − 176.5°C.

Analyzed as $C_{16}H_{18}N_2O_5$:
Calculated: C 60.37; H 5.70; N 8.80
Found: C 60.18; H 5.51; N 8.54

To 430 mg of methyl β-(5-hydroxyindolyl-3)-α-acetylaminopropionate was added 50 ml of 10% sulphuric acid and the reaction mixture was refluxed under heating for 10 hours. After condensation under reduced pressure to 15 ml volume, the reaction solution was unetralized with ammonia to pH 4, to afford the extract. The resulting extract was filtered and washed with water to afford 265 mg of 5-hydroxytryptophan in the yield of 78%.

We claim:
1. A thio-5-hydroxytryptophan derivative expressed by the following formula

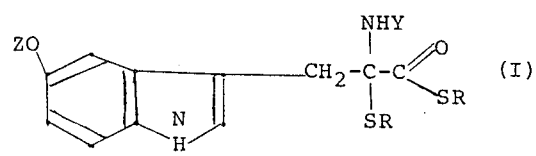

wherein R is alkyl having one to three carbon atoms, Y is acetyl, trifluoroacetyl, benzyloxycarbonyl or p-toluenesulfonyl and Z is methyl, benzyl, benzoyl or acetyl.

2. The compound of claim 1 in which R is a methyl group.

* * * * *